(12) United States Patent
Wang et al.

(10) Patent No.: US 11,485,729 B2
(45) Date of Patent: Nov. 1, 2022

(54) SUBSTITUTED PYRIDAZINONE COMPOUND

(71) Applicant: Shenzhen TargetRx, Inc., Guangdong (CN)

(72) Inventors: Yihan Wang, Guangdong (CN); Zhiqiang Liu, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/960,941

(22) PCT Filed: Jan. 17, 2019

(86) PCT No.: PCT/CN2019/072133
§ 371 (c)(1),
(2) Date: Jul. 9, 2020

(87) PCT Pub. No.: WO2019/144835
PCT Pub. Date: Aug. 1, 2019

(65) Prior Publication Data
US 2020/0347035 A1    Nov. 5, 2020

(30) Foreign Application Priority Data
Jan. 23, 2018 (CN) .......................... 201810063598.7

(51) Int. Cl.
*C07D 403/12* (2006.01)

(52) U.S. Cl.
CPC ................................ *C07D 403/12* (2013.01)

(58) Field of Classification Search
None
See application file for complete search history.

(56) References Cited

U.S. PATENT DOCUMENTS

| | | | | |
|---|---|---|---|---|
| 6,221,335 | B1 * | 4/2001 | Foster | C07B 59/002 424/1.81 |
| 7,807,672 | B2 * | 10/2010 | Deng | C07D 401/14 514/235.5 |
| 8,076,334 | B2 | 12/2011 | Haynes et al. | |
| RE46,024 | E * | 7/2016 | Haynes | C07D 237/18 514/247 |
| 2007/0197695 | A1 * | 8/2007 | Potyen | C08K 5/55 524/110 |
| 2013/0331382 | A1 * | 12/2013 | Hubbard | A61K 31/541 514/227.8 |

FOREIGN PATENT DOCUMENTS

| | | |
|---|---|---|
| CN | 101228135 A | 7/2008 |
| CN | 101801960 A | 8/2010 |
| CN | 105008335 A | 10/2015 |
| CN | 106008639 A | 10/2016 |
| CN | 111801324 A | 12/2019 |
| CN | 110627773 A | 10/2020 |
| JP | 2010-539209 A | 12/2010 |
| WO | 2007/009913 A1 | 1/2007 |
| WO | 2009/037172 A1 | 3/2009 |
| WO | 2014/043706 A1 | 3/2014 |

OTHER PUBLICATIONS

Dyck et al (Journal of Neurochemistry, 1986, 46, 399-404 (Year: 1986).*
Chinese First Office Action for Application No. 201910043782.X, dated Dec. 31, 2019.
International Search Report and Written Opinion for Application No. PCT/CN2019/072133, dated Apr. 17, 2019.
International Preliminary Report on Patentability for Application No. PCT/CN2019/072133, dated Aug. 6, 2020.
Jiang et al., Application of deuteration in drug research. Qilu Pharmaceutical Affairs. Dec. 31, 2010;29(11): 682-684.
Chinese Office Action for Application No. 202010556138.5, dated Jan. 6, 2021.
Extended European Search Report for Application No. EP19744170.2, dated Jan. 26, 2021.
No Author Listed, Precision Deuterium Chemistry Backgrounder. XP009169265. Concert Pharmaceuticals. Jan. 1, 2009; 1-6. Also available online at: http://concertpharma.com/about/documents/ConcertProductPlatformBackgrounder.pdf.
Dumont et al., Prospects in the use of deuterated molecules as therapeutic agents. Revue Ire, Institut National Des Radioelements, Belgium. Jan. 1, 1982; 6(4): 2-10. ISSN: 0770-1160.
Foster, Deuterium isotope effects in the metabolism of drugs and xenobiotics: implications for drug design, Chapter 1 to Chapter 2.1. Advances in Drug Research. Jan. 1, 1985;14: 1-40. ISSN:0065-2490.
Kelly et al., Discovery of 2-[3,5-dichloro-4-(5-isopropyl-6-oxo-1,6-dihydropyridazin-3-yloxy)phenyl]-3,5-dioxo-2,3,4,5-tetrahydro[1,2,4]triazine-6-carbonitrile (MGL-3196), a Highly Selective Thyroid Hormone Receptor β agonist in clinical trials for the treatment of dyslipidemia. J Med Chem. May 22, 2014;57(10):3912-23. doi: 10.1021/jm4019299. Epub Apr. 8, 2014.
Yarnell, Heavy-Hydrogen Drugs Turn Heads, Again. American Chemical Society. Jun. 22, 2009; 87(25):36-39. Retrieved from the Internet Oct. 21, 2009: URL: http://pubs.acs.org/cen/science/87/8725scil.html.

(Continued)

*Primary Examiner* — Brian J Davis

(74) *Attorney, Agent, or Firm* — Wolf, Greenfield & Sacks, P.C.

(57) ABSTRACT

The present invention relates to a pharmaceutical composition of a substituted pyridazinone compound and use thereof. The substituted pyridazinone compound is a compound as represented by formula (I), or a pharmaceutically acceptable salt, a prodrug, a hydrate or solvent compound, a crystalline form, and a stereoisomer or isotopic variant thereof. The compound is a THR-beta agonist which can be used for treating and/or preventing diseases regulated by thyroid hormone analogues.

Formula (I)

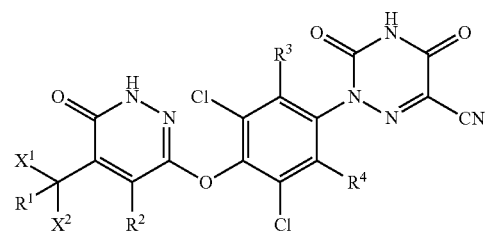

6 Claims, No Drawings

(56) References Cited

OTHER PUBLICATIONS

No Author Listed, Declaration Under 37 CFR 1.132 of Vinita Uttamsingh, dated Feb. 1, 2012. 3 pages.
Harbeson et al., Deuterium in Drug Discovery and Development. Ann Rep Med Chem. 2011; 46:403-417.
Shao et al., Derivatives of tramadol for increased duration of effect. Bioorg Med Chem Lett. Feb. 2006;16(3):691-4. doi: 10.1016/i.bmcl. 2005.10.024. Epub Oct. 27, 2005.
Japanese Office Action for Application No. 2020-540559, dated Sep. 14, 2021.
Buteau, Deuterated Drugs: Unexpectedly Nonobvious? J High Tech Law. 2009; X(1): 22-74.
Foster, Deuterium isotope effects in studies of drug metabolism. TIPS review. Dec. 1984; 5: 524-527.

\* cited by examiner

SUBSTITUTED PYRIDAZINONE COMPOUND

CROSS REFERENCE TO RELATED APPLICATIONS

The present application is a national application of PCT/CN2019/072133 filed on Jan. 17, 2019, which claims the priority of the Chinese Patent Application No. 201810063598.7 filed on Jan. 23, 2018. The Chinese Patent Application No. 201810063598.7 is incorporated herein by reference as part of the disclosure of the present application.

FIELD OF THE INVENTION

The present disclosure relates to the field of pharmaceutical technology, particularly relates to a substituted pyridazinone compound, a composition comprising the same and use thereof. More specifically, the present disclosure relates to some deuterated 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile compounds. These deuterated compounds can be used as THR-β agonists and for use in the treatment and/or prevention of diseases regulated by thyroid hormone analogues, with better pharmacokinetic properties.

BACKGROUND OF THE INVENTION

Thyroid hormone (TH) is produced by the thyroid and secreted into the circulatory system (hypothalamus/pituitary/thyroid system) in two different forms, which are 3,5,3',5'-tetraiodo-L-thyronine (T4) and 3,5,3'-triiodo-L-thyronine (T3). Although T4 is the main form secreted by the thyroid, T3 is a more physiologically active form. T4 is converted to T3 by tissue-specific deiodinase, which is present in all tissues, but mainly in liver and kidney.

The biological activity of the thyroid hormone is mediated by thyroid hormone receptors (TRs). TRs are encoded at two genomic loci (α and β) from the expression of different genes located on human chromosomes 17 and 3, respectively. Different protein subtypes are generated by selective cleavage of primary transcripts, and each gene produces two subtypes, namely TRα1, TRα2, TRβ1 and TRβ2. TRβ1 and TRβ2 are derived from the differential expression of the promoter, and these two subtypes only differ at the amino-terminus. TRα1 and TRα2 are derived from the differential splicing of the precursor mRNA, and mainly differ at the carboxyl-terminus. Among them, TRα1, TRβ1 and TRβ2 may bind to the thyroid hormone. It has been shown that the subtypes of thyroid hormone receptors may differ in their contribution to the specific physiological responses. TRβ1 plays an important role in the regulation of thyroid-stimulating hormone and thyroid hormone in liver, while TRβ2 plays a major role in the regulation of thyroid-stimulating hormone.

Thyroid hormone has the effect of lowering the low-density lipoprotein (LDL) in serum. Hyperthyroidism is associated with the low level of total serum cholesterol, which is attributed to the fact that the thyroid hormone increases the expression of LDL receptors in liver and stimulates the metabolism of cholesterol to bile acids. Hypothyroidism is associated with hypercholesterolemia, and thyroid hormone replacement therapy is known to lower the level of total cholesterol. The thyroid hormone may also reduce the risks of atherosclerosis and other cardiovascular diseases. The incidence of atherosclerotic vascular disease is directly related to the level of LDL cholesterol. The thyroid hormone has a beneficial effect on the obese patients by increasing the metabolic rate, oxygen consumption and heat release, thereby reducing the body weight and improving the co-morbidities associated with obesity, and may also have a beneficial effect on the blood glucose control in the obese patients with type 2 diabetes.

The development of thyroid analogues that avoid the adverse effects of hyperthyroidism and hypothyroidism while maintaining the beneficial effects of the thyroid hormone will open up new ways to treat patients with the following diseases: metabolic diseases such as obesity, hyperlipidemia, hypercholesterolemia, diabetes, other conditions such as hepatic steatosis, non-alcoholic steatohepatitis (NASH), atherosclerosis, cardiovascular disease, hypothyroidism, thyroid cancer, thyroid disease, and related conditions and diseases.

MGL-3196 (its chemical name is 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile), developed by Madrigal Pharmaceuticals, is a first-in-class, orally administered, small molecule and highly selective agonist of the liver thyroid hormone receptor β (THR-β). In a functional assay, the selectivity of MGL-3196 for THR-β over THR-α is approximately 28 times higher. Data of preclinical toxicology, clinical phase 1 and clinical phase II indicate that MGL-3196 has very attractive differential characteristics as a potential treatment for the non-alcoholic steatohepatitis (NASH) and dyslipidemia. By activating its receptor β (THR-β), the thyroid hormone plays a central role in controlling the lipid metabolism. Compared with the non-selective agonists, the high selectivity for THR-β enhances the safety of MGL-3196. MGL-3196 has no inhibitory effect on the central thyroid axis, nor on the heart rate or bone (the target tissue of THR-β agonists); at the same time, no increase of the liver enzymes has been observed. These safety characteristics make MGL-3196 one of the most promising potential drugs in this therapeutic field.

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism of many drugs, which could have been effective in treating diseases, could make them difficult to be used as drugs due to their rapid removal from the body. Although a frequent or high-dose administration may solve the problem of rapid drug clearance, this approach will bring problems such as poor compliance of patients, side effects caused by high-dose administration and increased treatment costs. In addition, drugs that are rapidly metabolized may also expose the patients to undesirable toxic or reactive metabolites.

Although MGL-3196 can effectively treat a variety of diseases as a THR-β agonist, it is still a challenging work to discover novel compounds with good oral bioavailability and drugability, having the beneficial effects of thyroid hormone while avoiding the adverse effects. Therefore, it is still necessary to develop THR-β agonists with better specific/pharmacodynamic/pharmacokinetic properties in this field. The present disclosure provides such compounds.

SUMMARY OF THE INVENTION

In view of the above technical problems, the present disclosure provides a novel deuterated pyridazinone compound, a composition comprising the same and use thereof.

The compounds have lower side effects, better pharmacodynamic/pharmacokinetic properties, and can be used as THR-β agonists in the treatment and/or prevention of related diseases regulated by thyroid hormone analogues.

As used herein, the term "compound of the present disclosure" (or "compound disclosed herein") refers to the compounds represented by formula (I). The term also includes pharmaceutically acceptable salts, prodrugs, hydrates, solvates, crystal forms, stereoisomers or isotopic variants of the compounds of formula (I).

In this regard, the technical solutions adopted by the present disclosure are as follows:

In the first aspect, the present disclosure provides a compound of formula (I):

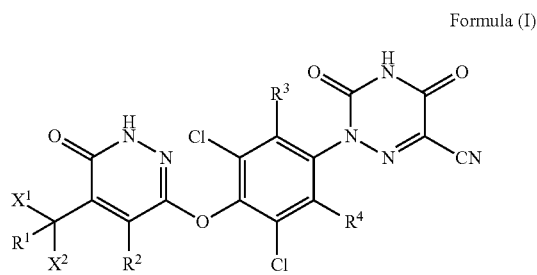

Formula (I)

wherein, $R^1$, $R^2$, $R^3$ and $R^4$ are independently selected from hydrogen or deuterium;

$X^1$ and $X^2$ are independently selected from $CH_3$, $CD_3$, $CHD_2$ or $CH_2D$;

with the proviso that if $X^1$ and $X^2$ are both $CH_3$, then at least one of $R^1$, $R^2$, $R^3$ and $R^4$ is deuterium.

In another aspect, the present disclosure provides a pharmaceutical composition, which comprises the compound of the present disclosure and pharmaceutically acceptable excipient(s). In a specific embodiment, the compound of the present disclosure is provided in an effective amount in the pharmaceutical composition. In a specific embodiment, the compound of the present disclosure is provided in a therapeutically effective amount. In a specific embodiment, the compound of the present disclosure is provided in a prophylactically effective amount.

In another aspect, the present disclosure provides a method of preparing the pharmaceutical composition described above, comprising the steps of: mixing the pharmaceutically acceptable excipient(s) with the compound of the present disclosure, thereby forming the pharmaceutical composition.

In another aspect, the present disclosure also provides a method of treating and/or preventing the disease regulated by thyroid hormone analogues in a subject. The method comprises administering to the subject a therapeutically effective amount of the compound disclosed herein. In a specific embodiment, the compound is administered orally, subcutaneously, intravenously or intramuscularly. In a specific embodiment, the compound is administered chronically. In a specific embodiment, the disease regulated by thyroid hormone analogues is selected from obesity, hyperlipidemia, hypercholesterolemia, diabetes, non-alcoholic steatohepatitis, atherosclerosis, cardiovascular disease, hypothyroidism or thyroid cancer.

Other objects and advantages of the present disclosure will be apparent to those skilled in the art from the subsequent specific embodiments, examples and claims.

DETAILED DESCRIPTION OF THE INVENTION

Definitions

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound wherein the content of the deuterium atom is not higher than the natural content of the deuterium isotope (0.015%).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and inorganic and organic bases.

Also disclosed herein are isotopically labeled compounds to the extent of the original compounds disclosed herein. Examples of isotopes that can be listed in compounds disclosed herein include hydrogen, carbon, nitrogen, oxygen, phosphorus, sulfur, fluorine and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. A compound disclosed herein containing the above isotope or other isotopic atoms, or an enantiomer, a diastereomer, an isomer, or a pharmaceutically acceptable salt or a solvate thereof are all within the scope disclosed herein. Certain isotopically labeled compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}C$, are easier to be prepared and detected and are the first choice for isotopes. Isotopically-labeled compounds can be prepared using the schemes shown in the Examples by conventional methods by replacing the non-isotopic reagents with readily available isotopically labeled reagents.

The compound disclosed herein may include one or more asymmetric centers, and thus may exist in a variety of "stereoisomer" forms, for example, enantiomeric and/or diastereomeric forms. For example, the compound disclosed herein may be in the form of an individual enantiomer, a diastereomer or a geometric isomer (e.g., cis- and trans-isomers), or may be in the form of a mixture of stereoisomers, including a racemic mixture and a mixture enriched in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

The compound disclosed herein may be in an amorphous or a crystalline form. In addition, the compound disclosed herein may exist in one or more crystalline forms. Therefore, the present disclosure includes all amorphous or crystalline forms of the compound disclosed herein within its scope. The term "crystal form" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

The term "solvate" refers to a complex in which a compound disclosed herein coordinates with a solvent molecule in a particular ratio. "Hydrate" refers to a complex formed by coordination of a compound disclosed herein with water.

The term "prodrug" as used herein refers to a compound, which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded compound disclosed herein which, when administered to a patient, releases the parent compound in vivo. A prodrug is typically prepared by modifying a functional group in such a way that the modification can be cleaved either by routine manipulation or decompose in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, the acetate/acetamide, formate/formamide and benzoate/benzamide derivatives of the hydroxyl, mercapto and amino functional groups of the compound of formula (I). Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those, which readily decompose in a human body to release a parent acid or its salt.

In a specific embodiment, the prodrug of the compound of formula (I) is a compound of formula (A):

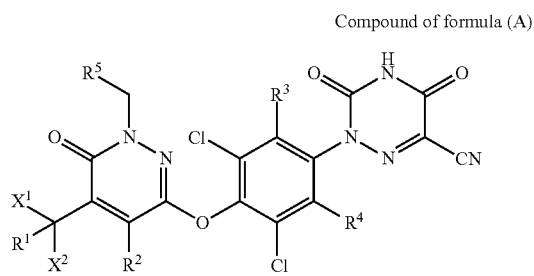

Compound of formula (A)

wherein,
$R^1$, $R^2$, $R^3$ and $R^4$ are independently selected from hydrogen or deuterium;

$X^1$ and $X^2$ are independently selected from $CH_3$, $CD_3$, $CHD_2$ or $CH_2D$;

$R^5$ is selected from —OH, —O-linked amino acid, —OP(O)(OH)$_2$, OC(O)CH[CH(CH$_3$)$_2$]NH$_2$, OC(O)CH[CH(CH$_3$)(CH$_2$CH$_3$)]NH$_2$, OC(O)CH(CH$_3$)NH$_2$, methyl, ethyl, cyclopentyl, morpholinyl, —CH$_2$-morpholinyl, —CH$_2$—N-methylpiperazinyl, phenyl, pyrazinyl, pyrimidinyl or pyridyl;

with the proviso that if $X^1$ and $X^2$ are both $CH_3$, then at least one of $R^1$, $R^2$, $R^3$ and $R^4$ is deuterium.

As used herein, the term "O-linked amino acid" refers to any natural or synthetic amino acid that is attached to the molecule via the oxygen of the carboxyl group of the amino acid, preferably via the carboxyl group at the carboxyl-terminus of the amino acid. Preferred examples of the amino acid are (S)-2-amino-3-methyl-butyric acid, (2S,3S)-2-amino-3-methyl-valeric acid and (S)-2-amino-propionic acid.

As used herein, the term "subject" includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

"Disease", "disorder" and "condition" are used interchangeably herein.

As used herein, and unless otherwise specified, the terms "treat", "treating", and "treatment" contemplate an action that occurs while a subject is suffering from a particular disease, disorder, or condition, which reduces the severity of the disease, disorder or condition, or retards or slows the progression of the disease, disorder or condition ("therapeutic treatment"). The term also contemplates an action that occurs before a subject begins to suffer from a specific disease, disorder or condition ("prophylactic treatment").

Generally, the "effective amount" of a compound refers to an amount sufficient to elicit a desired biological response. As will be appreciated by those skilled in the art, the effective amount of the compound disclosed herein can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

As used herein, and unless otherwise specified, the "therapeutically effective amount" of the compound is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

As used herein, and unless otherwise specified, the "prophylactically effective amount" of the compound is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the therapeutic agents disclosed herein. For example, the compounds of the present disclosure can be administered simultaneously or sequentially in separate unit dosage with other therapeutic agents, or simultaneously in a single unit dosage with other therapeutic agents.

Specific Embodiments

Compounds

The present disclosure provides a compound of formula (I), or a pharmaceutically acceptable salt, prodrug, hydrate, solvate, crystal form, stereoisomer or isotopic variant thereof:

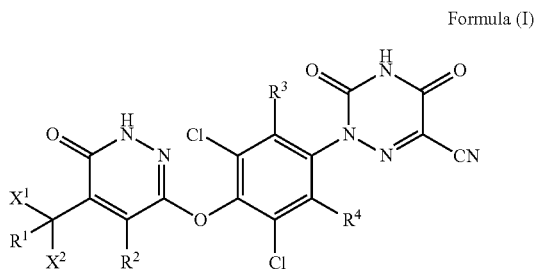

Formula (I)

wherein,
$R^1$, $R^2$, $R^3$ and $R^4$ are independently selected from hydrogen or deuterium;
$X^1$ and $X^2$ are independently selected from $CH_3$, $CD_3$, $CHD_2$ or $CH_2D$;
with the proviso that if $X^1$ and $X^2$ are both $CH_3$, then at least one of $R^1$, $R^2$, $R^3$ and $R^4$ is deuterium.

As an alternative embodiment of the present disclosure, the compound of formula (I) contains at least one deuterium atom, alternatively one deuterium atom, alternatively two deuterium atoms, alternatively three deuterium atoms, alternatively four deuterium atoms, alternatively five deuterium atoms, alternatively six deuterium atoms, alternatively seven deuterium atoms, alternatively eight deuterium atoms, alternatively nine deuterium atoms, and alternatively ten deuterium atoms.

As an alternative embodiment of the present disclosure, the content of deuterium isotope in each deuterated position is at least greater than the natural content of deuterium isotope (0.015%), alternatively greater than 30%, alternatively greater than 50%, alternatively greater than 75%, alternatively greater than 95%, and alternatively greater than 99%.

Specifically, in the present disclosure, the content of the deuterium isotope in each deuterated position of $R^1$, $R^2$, $R^3$, $R^4$, $X^1$ and $X^2$ is at least 5%, alternatively greater than 10%, alternatively greater than 15%, alternatively greater than 20%, alternatively greater than 25%, alternatively greater than 30%, alternatively greater than 35%, alternatively greater than 40%, alternatively greater than 45%, alternatively greater than 50%, alternatively greater than 55%, alternatively greater than 60%, alternatively greater than 65%, alternatively greater than 70%, alternatively greater than 75%, alternatively greater than 80%, alternatively greater than 85%, alternatively greater than 90%, alternatively greater than 95%, and alternatively greater than 99%.

In another specific embodiment, among $R^1$, $R^2$, $R^3$, $R^4$, $X^1$ and $X^2$ of the compound of formula (I), at least one of them contains deuterium, alternatively two contain deuterium, alternatively three contain deuterium, alternatively four contain deuterium, alternatively five contain deuterium, alternatively six contain deuterium, alternatively seven contain deuterium, alternatively eight contain deuterium, alternatively nine contain deuterium, and alternatively ten contain deuterium. Specifically, the compound of formula (I) contains at least one, two, three, four, five, six, seven, eight, nine and ten deuterium atoms.

As an alternative embodiment of the present disclosure, $X^1$ and $X^2$ are independently selected from $CH_3$, $CD_3$, $CHD_2$ or $CH_2D$; in another specific embodiment, $X^1$ is $CH_3$; in another specific embodiment, $X^1$ is $CD_3$; in another specific embodiment, $X^1$ is $CH_2D$; in another specific embodiment, $X^1$ is $CHD_2$; in another specific embodiment, $X^2$ is $CH_3$; in another specific embodiment, $X^2$ is $CD_3$; in another specific embodiment, $X^2$ is $CH_2D$; in another specific embodiment, $X^2$ is $CHD_2$; in another specific embodiment, $X^1$ is $CH_3$, $X^2$ is $CD_3$; in another specific embodiment, $X^1$ is $CD_3$, $X^2$ is $CH_3$; in another specific embodiment, $X^1$ is $CH_3$, $X^2$ is $CH_3$; in another specific embodiment, $X^1$ is $CD_3$, $X^2$ is $CD_3$.

As an alternative embodiment of the present disclosure, $R^1$ is selected from hydrogen or deuterium; in another specific embodiment, $R^1$ is hydrogen; in another specific embodiment, $R^1$ is deuterium.

As an alternative embodiment of the present disclosure, $R^2$, $R^3$ and $R^4$ are independently selected from hydrogen or deuterium; in another specific embodiment, $R^2$ is hydrogen; in another specific embodiment, $R^2$ is deuterium; in another specific embodiment, $R^3$ is hydrogen; in another specific embodiment, $R^3$ is deuterium; in another specific embodiment, $R^4$ is hydrogen; in another specific embodiment, $R^4$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^2$ is hydrogen, $R^1$, $R^3$ and $R^4$ are independently selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then at least one of $R^1$, $R^3$ and $R^4$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^2$ is hydrogen, $R^1$, $R^3$ and $R^4$ are independently selected from hydrogen or deuterium, $X^1$ and $X^2$ are independently selected from $CH_3$ or $CD_3$, with the proviso that if $X^1$ and $X^2$ are both $CH_3$, then at least one of $R^1$, $R^3$ and $R^4$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^1$ is hydrogen, $R^2$, $R^3$ and $R^4$ are independently selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then at least one of $R^2$, $R^3$ and $R^4$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^1$ is hydrogen, $R^2$, $R^3$ and $R^4$ are independently selected from hydrogen or deuterium, $X^1$ and $X^2$ are independently selected from $CH_3$ or $CD_3$, with the proviso that if $X^1$ and $X^2$ are both $CH_3$, then at least one of $R^2$, $R^3$ and $R^4$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^1$ and $R^2$ are hydrogen, $R^3$ and $R^4$ are independently selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then at least one of $R^3$ and $R^4$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^1$ and $R^2$ are hydrogen, $R^3$ and $R^4$ are independently selected from hydrogen or deuterium, $X^1$ and $X^2$ are independently selected from $CH_3$ or $CD_3$, with the proviso that if $X^1$ and $X^2$ are both $CH_3$, then at least one of $R^3$ and $R^4$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^3$ and $R^4$ are hydrogen, $R^1$ and $R^2$ are independently selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then at least one of $R^1$, $R^3$ and $R^4$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^3$ and $R^4$ are hydrogen, $R^1$ and $R^2$ are independently selected from hydrogen or deuterium, $X^1$ and $X^2$ are independently selected from $CH_3$ or $CD_3$, with the proviso that if $X^1$ and $X^2$ are both $CH_3$, then at least one of $R^1$, $R^3$ and $R^4$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^2$, $R^3$ and $R^4$ are hydrogen, $R^1$ is selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then at least one of $R^1$ and $R^2$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^2$, $R^3$ and $R^4$ are hydrogen, $R^1$ is selected from hydrogen or deuterium, $X^1$ and $X^2$ are independently selected from $CH_3$ or $CD_3$, with the proviso that if $X^1$ and $X^2$ are both $CH_3$, then at least one of $R^1$ and $R^2$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^1$, $R^3$ and $R^4$ are hydrogen, $R^2$ is selected from hydrogen or deuterium, $X^1$ and $X^2$ are independently selected from $CH_3$, $CD_3$, $CHD_2$ or $CH_2D$, with the proviso that if $X^1$ and $X^2$ are both $CH_3$, then $R^1$ is deuterium.

In another specific embodiment, the present disclosure provides a compound of formula (I), or a pharmaceutically acceptable salt, prodrug, hydrate, solvate, crystal form, stereoisomer or isotopic variant thereof, wherein, $R^1$, $R^3$ and $R^4$ are hydrogen, $R^2$ is selected from hydrogen or deuterium, $X^1$ and $X^2$ are independently selected from $CH_3$ or $CD_3$, with the proviso that if $X^1$ and $X^2$ are both $CH_3$, then $R^1$ is deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $R^1$, $R^2$, $R^3$ and $R^4$ are hydrogen, $X^1$ and $X^2$ are independently selected from $CH_3$, $CD_3$, $CHD_2$ or $CH_2D$, with the proviso that $X^1$ and $X^2$ are not both $CH_3$.

In another specific embodiment, the present disclosure provides a compound of formula (I), or a pharmaceutically acceptable salt, prodrug, hydrate, solvate, crystal form, stereoisomer or isotopic variant thereof, wherein, $R^1$, $R^2$, $R^3$ and $R^4$ are hydrogen, $X^1$ and $X^2$ are independently selected from $CH_3$ or $CD_3$, with the proviso that $X^1$ and $X^2$ are not both $CH_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^2$, $R^3$ and $R^4$ are independently selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^2$, $R^3$ and $R^4$ are independently selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^2$ is hydrogen, $R^1$, $R^3$ and $R^4$ are independently selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^2$ is hydrogen, $R^1$, $R^3$ and $R^4$ are independently selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$ is hydrogen, $R^2$, $R^3$ and $R^4$ are independently selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$ is hydrogen, $R^2$, $R^3$ and $R^4$ are independently selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$ and $R^2$ are hydrogen, $R^3$ and $R^4$ are independently selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$ and $R^2$ are hydrogen, $R^3$ and $R^4$ are independently selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^3$ and $R^4$ are hydrogen, $R^1$ and $R^2$ are independently selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^3$ and $R^4$ are hydrogen, $R^1$ and $R^2$ are independently selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^3$ and $R^4$ are hydrogen, $R^2$ is selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^3$ and $R^4$ are hydrogen, $R^2$ is selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^2$, $R^3$ and $R^4$ are hydrogen, $R^1$ is selected from hydrogen or deuterium, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^2$, $R^3$ and $R^4$ are hydrogen, $R^1$ is selected from hydrogen or deuterium, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^2$, $R^3$ and $R^4$ are hydrogen, $X^2$ is selected from $CH_3$, $CD_3$, $CHD_2$ or $CH_2D$.

In another specific embodiment, the present disclosure provides a compound of formula (I), or a pharmaceutically acceptable salt, prodrug, hydrate, solvate, crystal form, stereoisomer or isotopic variant thereof, wherein, $X^1$ is $CD_3$, $R^1$, $R^2$, $R^3$ and $R^4$ are hydrogen, $X^2$ is selected from $CH_3$ or $CD_3$.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^1$, $R^2$, $R^3$ and $R^4$ are independently selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^2$ is hydrogen, $R^1$, $R^3$ and $R^4$ are independently selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^1$ is hydrogen, $R^2$, $R^3$ and $R^4$ are independently selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^1$ and $R^2$ are hydrogen, $R^3$ and $R^4$ are independently selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^3$ and $R^4$ are hydrogen, $R^1$ and $R^2$ are independently selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^1$, $R^3$ and $R^4$ are hydrogen, $R^2$ is selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^2$, $R^3$ and $R^4$ are hydrogen, $R^1$ is selected from hydrogen or deuterium.

As an alternative embodiment of the present disclosure, the present disclosure provides a compound of formula (I), or a pharmaceutically acceptable salt, prodrug, hydrate, solvate, crystal form, stereoisomer or isotopic variant thereof, wherein, $X^1$ and $X^2$ are $CD_3$, $R^1$, $R^2$, $R^3$ and $R^4$ are hydrogen.

As an alternative embodiment of the present disclosure, the present disclosure relates to a compound described above, which is of formula (Ia):

Formula (Ia)

wherein,
$R^1$ is selected from hydrogen or deuterium;
$X^1$ and $X^2$ are independently selected from $CH_3$, $CD_3$, $CHD_2$ or $CH_2D$;
with the proviso that if $X^1$ and $X^2$ are both $CH_3$, then $R^1$ is deuterium.

As an alternative embodiment of the present disclosure, the present disclosure relates to a compound described above, which is of formula (Ia):

Formula (Ia)
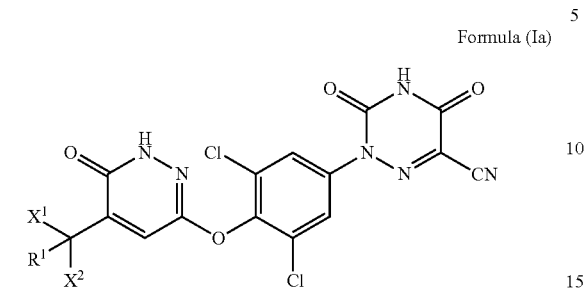

wherein,

R¹ is selected from hydrogen or deuterium;
X¹ and X¹ are independently selected from CH₃ or CD₃;
with the proviso that if X¹ and X¹ are both CH₃, then R¹ is deuterium.

As an alternative embodiment of the present disclosure, the compound is selected from the following group of compounds:

Formula (1)
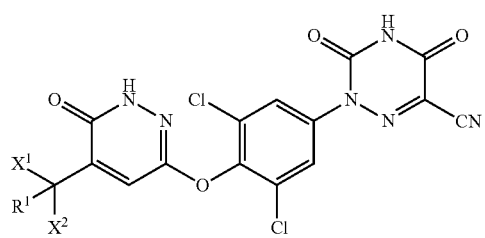

Formula (2)
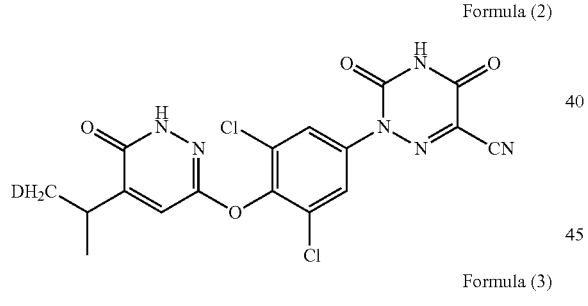

Formula (3)
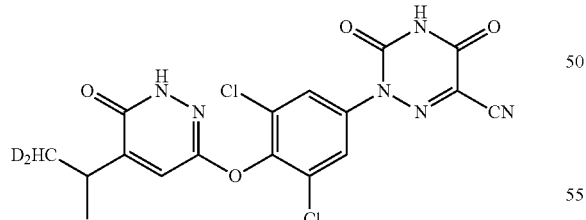

Formula (4)
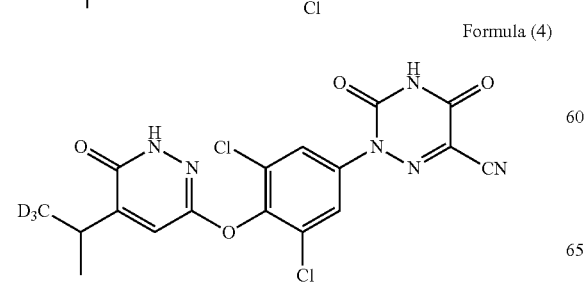

Formula (5)
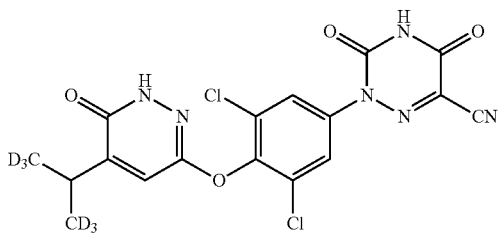

Formula (6)
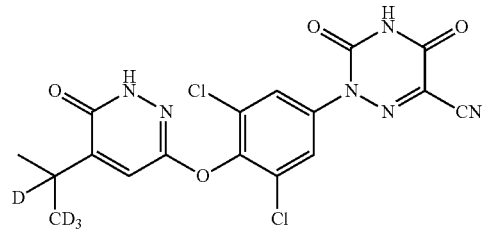

Formula (7)
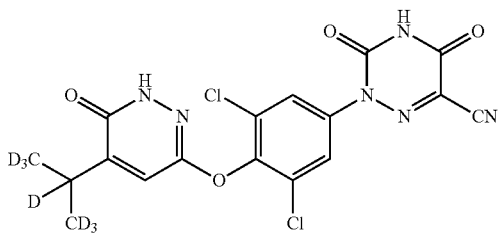

Formula (8)
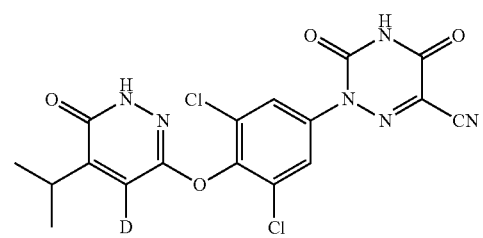

Formula (9)
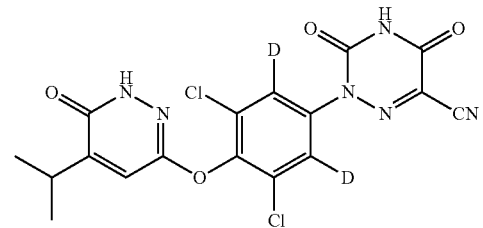

Formula (10)
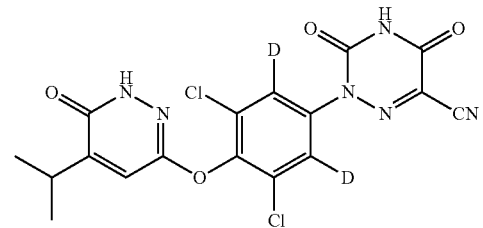

Formula (11)
Formula (12)
Formula (13)
Formula (14)
Formula (15)
Formula (16)
Formula (17)
Formula (18)
Formula (19)
Formula (20)
Formula (21)
Formula (22)

-continued

Formula (23)

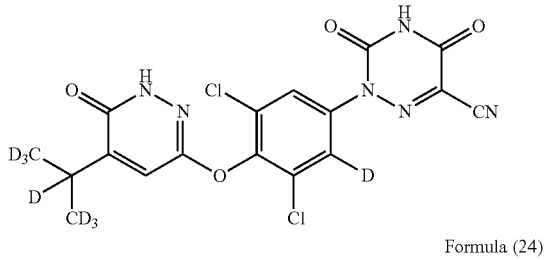

Formula (24)

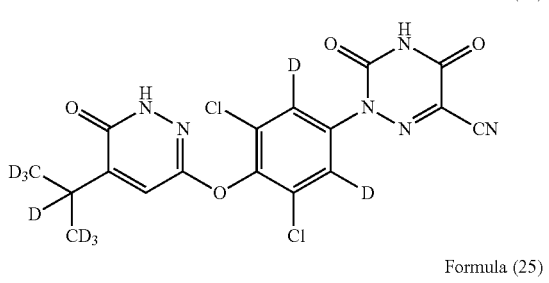

Formula (25)

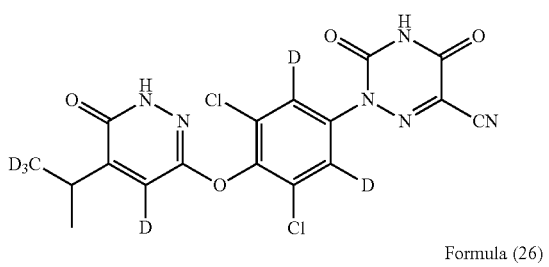

Formula (26)

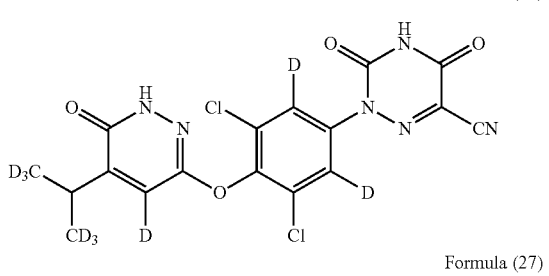

Formula (27)

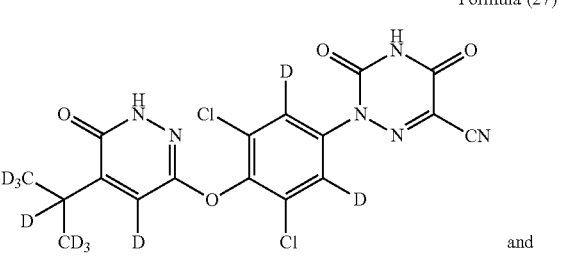

and
Formula (28)

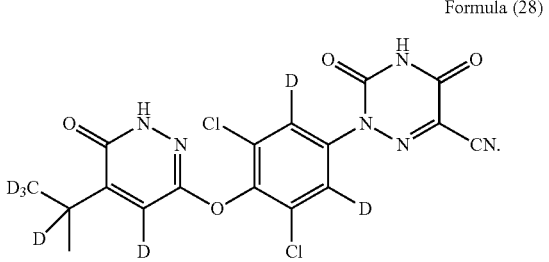

As an alternative embodiment of the present disclosure, the compounds do not include the non-deuterated compounds.

It is to be understood that the compounds of formula (I) disclosed herein may be derivatized at the functional groups to obtain the derivatives that can be converted back to the parent compounds in vivo.

Pharmaceutical Compositions and Methods of Administration

In another aspect, provided herein is a pharmaceutical composition comprising the compound disclosed herein (also referred to as "active component") and pharmaceutically acceptable excipient(s). In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

The pharmaceutical composition disclosed herein comprises a safe and effective amount of the compound disclosed herein, or a pharmacologically acceptable salt thereof, and pharmacologically acceptable excipient(s) or carrier(s). By "safe and effective amount" it is meant that the amount of the compound is sufficient to significantly improve the condition without causing serious side effects. In general, the pharmaceutical composition contains from 0.5 to 2000 mg of the compound disclosed herein per dose, more preferably from 1 to 500 mg of the compound disclosed herein per dose. Preferably, the "one dose" is one capsule or tablet.

The "pharmaceutically acceptable excipient" refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The pharmaceutical composition disclosed herein can be prepared by combining the compound disclosed herein with suitable pharmaceutically acceptable excipient(s), for example, as a solid, semi-solid, liquid or gaseous preparation such as tablets, pills, capsules, powders, granules, ointments, emulsions, suspensions, solutions, suppositories, injections, inhalants, gels, microspheres, aerosols and the like.

Typical routes of administration of the compound disclosed herein or a pharmaceutical composition thereof include, but are not limited to, oral, rectal, transmucosal, enteral administration, or topical, transdermal, inhalation, parenteral, sublingual, intravaginal, intranasal, intraocular, intraperitoneal, intramuscular, subcutaneous, intravenous administration.

The pharmaceutical composition disclosed herein can be produced by a method well known in the art, such as a conventional mixing method, a dissolution method, a granulation method, a sugarcoating pill method, a grinding method, an emulsification method, a freeze drying method, and the like.

For oral administration, the pharmaceutical composition can be formulated by mixing the active compound with pharmaceutically acceptable excipient(s) which are well known in the art. These excipients enable the compound disclosed herein to be formulated into tablets, pills, troches, dragees, capsules, liquids, gels, slurries, suspensions and the like for oral administration to a patient.

A solid oral composition can be prepared by a conventional mixing, filling or tabletting method. For example, it can be obtained by mixing the active compound with solid excipient(s), optionally milling the resulting mixture, adding other suitable adjuvant(s) if necessary, and then processing the mixture into granules, thereby obtaining a tablet or a core of dragee. Suitable excipients include, but are not limited to, binders, diluents, disintegrants, lubricants, glidants, sweeteners or flavoring agents, and the like, such as microcrystalline cellulose, glucose solution, acacia mucilage, gelatin solution, sucrose and starch paste; talc, starch, calcium stearate or stearic acid; lactose, sucrose, starch, mannitol, sorbitol or dicalcium phosphate; silica; cross-linked hydroxymethylcellulose sodium, pregelatinized starch, sodium starch glycolate, alginic acid, corn starch, potato starch, methyl cellulose, agar, hydroxymethyl cellulose, cross-linked polyvinyl pyrrolidone and the like. The core of the dragee may optionally be coated according to methods well known in the ordinary pharmaceutical practice, especially using enteric coatings.

The pharmaceutical compositions may also be suitable for parenteral administration, such as sterile solutions, suspensions or lyophilized products in a suitable unit dosage form. Suitable excipients such as fillers, buffers or surfactants can be used.

The compounds disclosed herein may be administered by any route and method of administration, for example by oral or parenteral (e.g., intravenous) administration. A therapeutically effective amount of the compound disclosed herein is from about 0.0001 to 20 mg/kg body weight per day, such as from 0.001 to 10 mg/kg body weight per day.

The dosing frequency of the compounds disclosed herein is determined by the needs of the individual patient, for example, once or twice daily, or more times per day. Administration may be intermittent, for example, wherein the patient receives a daily dose of the compound disclosed herein for a period of several days, and then the patient does not receive a daily dose of the compound disclosed herein for a period of several days or more.

Therapeutic Indications of the Compound Disclosed Herein

The novel compounds of the present disclosure are thyroid hormone analogues. Therefore, the compounds of the present disclosure can be used in the treatment and/or prevention of diseases regulated by thyroid hormone analogues, especially metabolic diseases, such as obesity, hyperlipidemia, hypercholesterolemia and diabetes, and can be used in other diseases such as NASH (non-alcoholic steatohepatitis), atherosclerosis, cardiovascular disease, hypothyroidism, thyroid cancer, and related conditions and diseases. Obese patients are those with a body mass index of greater than 25.

In another specific embodiment, the present disclosure relates to a method of treating and/or prophylactically treating the diseases regulated by thyroid hormone analogues, in particular metabolic diseases such as obesity, hyperlipidemia, hypercholesterolemia and diabetes, as well as NASH (non-alcoholic steatohepatitis), atherosclerosis, cardiovascular disease, hypothyroidism, thyroid cancer, and related conditions and diseases. The method comprises administering the compounds as defined above to a human or an animal Preferably, the amount of the compounds administered is from about 0.01 mg/kg to about 50 mg/kg per day, more preferably from about 0.3 mg/kg to about 10 mg/kg per day, and more preferably from about 0.70 mg/kg to about 3.5 mg/kg per day.

The present disclosure also includes a use of the compounds as defined above in the treatment and/or prophylactic treatment of diseases regulated by thyroid hormone analogues, especially metabolic diseases such as obesity, hyperlipidemia, hypercholesterolemia and diabetes, as well as NASH (non-alcoholic steatohepatitis), atherosclerosis, cardiovascular disease, hypothyroidism, thyroid cancer, and related conditions and diseases.

The present disclosure also relates to a use of the compounds as described above in the preparation of a medicament for the treatment and/or prophylactic treatment of diseases regulated by thyroid hormone analogues, especially metabolic diseases such as obesity, hyperlipidemia, hypercholesterolemia and diabetes, as well as NASH (non-alcoholic steatohepatitis), atherosclerosis, cardiovascular disease, hypothyroidism, thyroid cancer, and related conditions and diseases. This medicament contains the compounds as described above. NASH is also more preferred.

Prevention and/or treatment of the metabolic diseases are the preferred indications. Diabetes is more preferred, especially non-insulin-dependent diabetes (type 2). Obesity is also more preferred. Hyperlipidemia is also more preferred, especially hypercholesterolemia.

Compared with the non-deuterated compounds known in the prior art, the compounds of the present disclosure have a series of advantages. The advantages of the present disclosure include: first, the compounds and compositions of the technical solutions disclosed herein provide a more advantageous therapeutic tool for the treatment and/or prevention of diseases regulated by thyroid hormone analogues. Second, the metabolism of the compound in the organism is improved, allowing the compound to have better pharmacokinetic parameters. In this case, the dose may be changed and a long-acting formulation may be formed to improve the applicability. Third, the drug concentration of the compound in animals is increased, so that the efficacy of the drug is improved. Fourth, the safety of the compound may be increased due to the inhibition of certain metabolites.

EXAMPLES

The present disclosure is further illustrated below in conjunction with specific examples. It is to be understood that the examples are used to illustrate the present disclosure, and not intended to limit the scope of present disclosure. In the following examples, the experimental methods wherein the particular conditions are not specified are usually in accordance with conventional conditions or according to the conditions recommended by the manufacturer. Parts and percentages are parts by weight and percentage by weight unless otherwise stated.

Usually, in the preparation process, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1 Preparation of 2-(3,5-dichloro-4-((6-oxo-5-(propan-2-yl-1,1,1-d₃)-1,6-dihydropyridazin-3-yl)oxy)phenyl)-3,5-dioxo-2,3,4,5-tetrahydro-1,2,4-triazine-6-carbonitrile (Compound M-1)

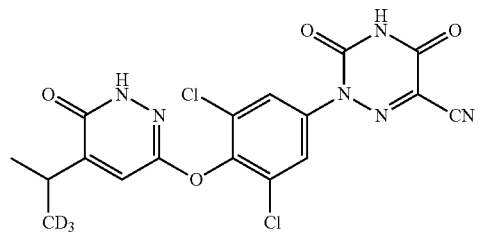

The following route was used for the synthesis:

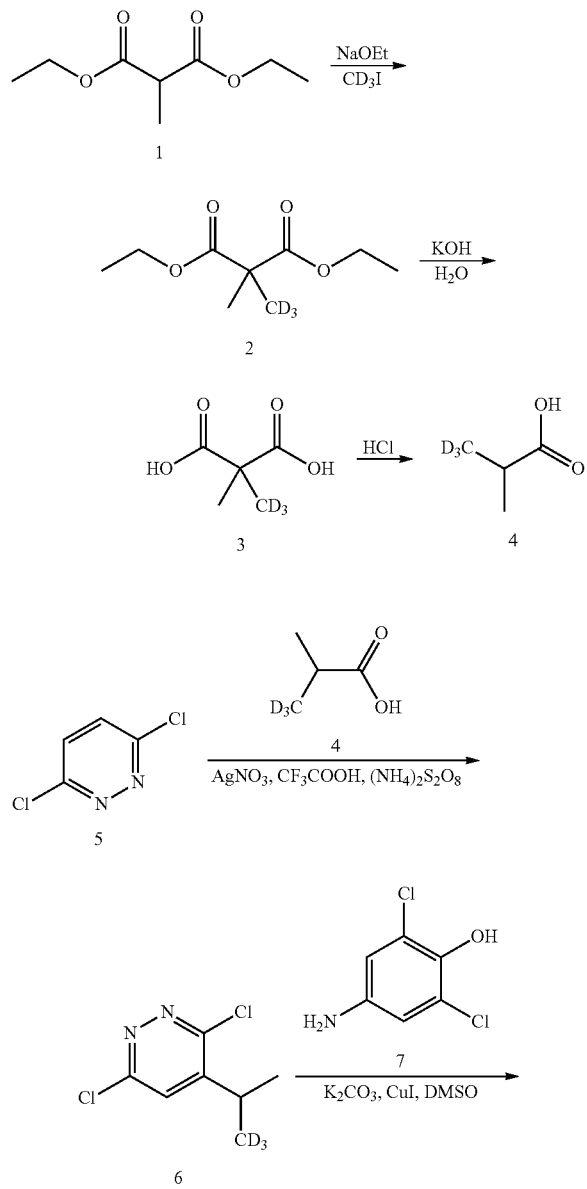

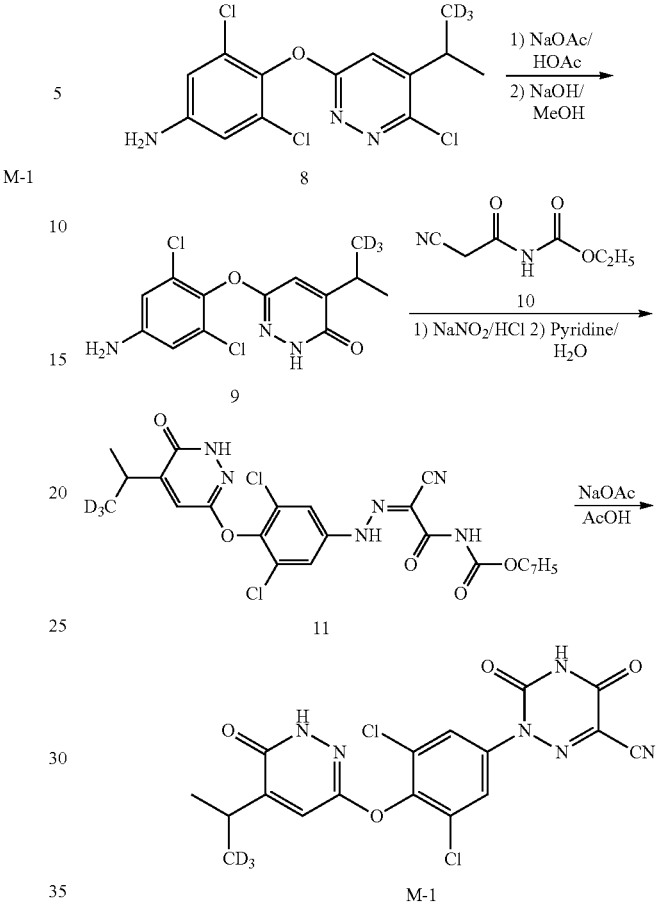

Step 1 Synthesis of Compound 2

Compound 1 (5.5 g, 31.6 mmol) and sodium ethoxide (2.6 g, 37.9 mmol) were sequentially added to ethanol (30 ml). After stirring at 70° C. for 0.5 h, the resulting solution was cooled to room temperature. Then deuterated iodomethane (5.0 g, 34.7 mmol) was slowly added dropwise to the solution described above, and the reaction solution was stirred and reacted at room temperature for 20 h. Most of the solvent was removed, and the residue was extracted with dichloromethane (40 ml×2). The organic phases were combined, and dried over anhydrous sodium sulfate. The solvent was removed to give 5.1 g of brownish red oil, with a yield of 85%.

Step 2 Synthesis of Compound 3

Potassium hydroxide (4.4 g, 78.4 mmol) was added to a solution of compound 2 (5.0 g, 26.1 mmol) in water (20 ml). After refluxing at 100° C. for 3 h, the reaction solution was cooled to room temperature. The pH value of the reaction was adjusted to around 2 with concentrated hydrochloric acid. Most of the water was dried with a rotary evaporator, and the residue was extracted with acetone (50 ml×3). The organic phases were combined, and dried over anhydrous sodium sulfate. The solvent was removed to give 2.6 g of an off-white solid, with a yield of 74%.

Step 3 Synthesis of Compound 4

At room temperature, concentrated hydrochloric acid (40 ml) was slowly added to compound 3 (2.6 g, 19.3 mmol), and the resulting solution was heated to 100° C. and refluxed for 12 h. The reaction solution was extracted with dichloromethane (50 ml×3). The organic phases were combined, and dried over anhydrous sodium sulfate. The solvent was removed to give 0.7 g of brown oil, with a yield of 41%.

Step 4 Synthesis of Compound 6

Silver nitrate (0.075 g, 0.436 mmol), compound 4 (0.571 g, 6.10 mmol) and trifluoroacetic acid (0.1 ml) were sequentially added to a solution of compound 5 (0.65 g, 4.36 mmol) in water (20 ml), and the reaction solution was heated to 70° C. Then a solution of ammonium persulfate ($(NH_4)_2S_2O_8$, 2.0 g, 8.72 mmol, 10 ml) in water was slowly added dropwise, after which, the resulting mixture was reacted for 0.5 h, and extracted with dichloromethane (30 ml×3). The organic phases were combined, and dried over anhydrous sodium sulfate. The solvent was removed to give 0.65 g of oil, with a yield of 77%. LC-MS (APCI): m/z=194.23 (M+1)$^+$.

Step 5 Synthesis of Compound 8

Compound 6 (0.9 g, 4.63 mmol), compound 7 (0.82 g, 4.63 mmol), copper(I) iodide (0.53 g, 2.78 mmol) and potassium carbonate (2.60 g, 18.52 mmol) were sequentially added to DMSO (20 ml), and the reaction solution was reacted at 90° C. for 20 h. After cooling to room temperature, water (50 ml) was added to quench the reaction, and the resulting mixture was extracted with ethyl acetate (60 ml×3). The organic phases were combined, and dried over anhydrous sodium sulfate. The solvent was removed, and the concentrate was separated by column (eluent: petroleum ether/ethyl acetate (v/v)=5:1) to give 1.2 g of an off-white solid, with a yield of 75%. LC-MS (APCI): m/z=335.59 (M+1)$^+$.

Step 6 Synthesis of Compound 9

Sodium acetate (0.49 g, 6.00 mmol) was added to a solution of compound 8 (1.0 g, 3.00 mmol) in acetic acid (20 ml), and the reaction solution was reacted at 100° C. for 10 h. After cooling to room temperature, most of the solvent was dried with a rotary evaporator, and the resulting solution was extracted with ethyl acetate (30 ml×2). The organic phases were combined, dried over anhydrous sodium sulfate, and dried with a rotary evaporator to give an intermediate. Then, sodium hydroxide (20 ml, 1 mol/L) and methanol (20 ml) were added, and the reaction solution was refluxed for 12 h. After cooling to room temperature, most of the solvent was removed, and the pH was adjusted to 5 with dilute hydrochloric acid. Ethyl acetate (30 ml×2) was added for extraction. The organic phases were combined, and the concentrate was separated by column (eluent: petroleum ether/ethyl acetate (v/v)=1:1) to give 0.8 g of an off-white solid, with a yield of 85%. LC-MS (APCI): m/z=317.06 (M+1)$^+$.

Step 7 Synthesis of Compound 11

Compound 9 (0.5 g, 1.58 mmol) and concentrated hydrochloric acid (7 ml) were sequentially added to water (15 ml). The resulting solution was cooled to 0° C., to which a solution of sodium nitrite (0.143 g, 2.05 mmol, 2 ml) in water was slowly added dropwise, and reacted for 0.5 h. In another reactor, compound 10 (0.246 g, 1.58 mmol), pyridine (5 ml) and water (15 ml) were added, and the resulting solution was cooled to 0° C. Then, the reaction solution in the previous reactor was quickly poured into it, stirred and reacted for 0.5 h. After the reaction was completed, ethyl acetate (30 ml×2) was added for extraction. The organic phases were combined, dried, and dried with a rotary evaporator to give 0.56 g of an orange solid, with a yield of 74%. LC-MS (APCI): m/z=484.36 (M+1)$^+$. $^1$H NMR (500 MHz, DMSO) 12.21 (s, 1H), 10.99 (s, 2H), 7.99 (s, 2H), 7.36 (s, 1H), 4.19 (q, J=7.1 Hz, 2H), 3.01 (d, J=6.7 Hz, 1H), 1.17 (s, 6H).

Step 8 Synthesis of Compound M-1

Sodium acetate (0.42 g, 5.15 mmol) was added to a solution of compound 11 (0.5 g, 1.03 mmol) in acetic acid (15 ml), and the reaction solution was reacted at 120° C. for 2 h. After cooling to room temperature, most of the solvent was dried with a rotary evaporator. A small amount of water was added and ethyl acetate (20 ml×2) was added for extraction. The organic phases were combined, dried over anhydrous sodium sulfate, and dried with a rotary evaporator to give a crude product. Then activated carbon (0.5 g) and acetonitrile (20 ml) were added, and refluxed for 2 hours. The resulting mixture was cooled, filtered, and dried with a rotary evaporator to give 0.21 g of a product, with a yield of 46%. LC-MS (APCI): m/z=438.21 (M+1)$^+$. $^1$H NMR (500 MHz, DMSO) δ 13.21 (s, 1H), 12.19 (s, 1H), 7.89 (s, 2H), 7.46 (s, 1H), 3.19 (m, 1H), 1.17 (d, 3H).

Example 2 Preparation of 2-(3,5-dichloro-4-((6-oxo-5-(propan-2-yl-1,1,1,3,3,3-d$_6$)-1,6-dihydro-pyridazin-3-yl)oxy)phenyl)-3,5-dioxo-2,3,4,5-tetrahydro-1,2,4-triazine-6-carbonitrile (Compound M-2)

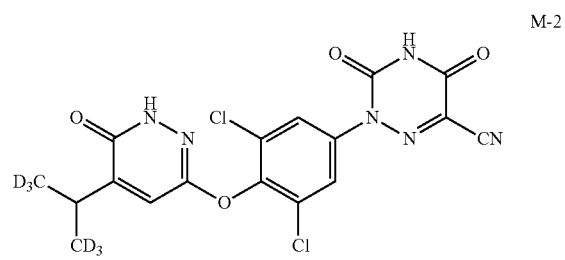 [SMILES: [2H]C([2H])([2H])C(c1cc(Oc2c(Cl)cc(-n3nc(C#N)c(=O)[nH]c3=O)cc2Cl)n[nH]c1=O)C([2H])([2H])[2H]]

The following route was used for the synthesis:

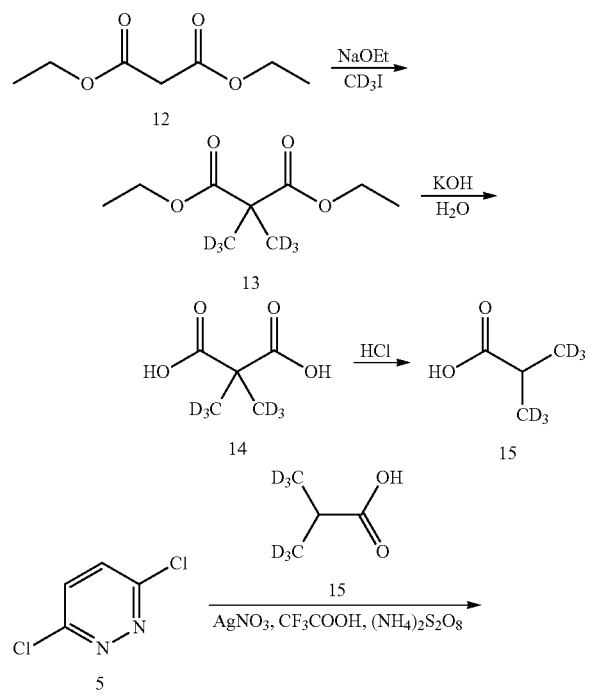

-continued

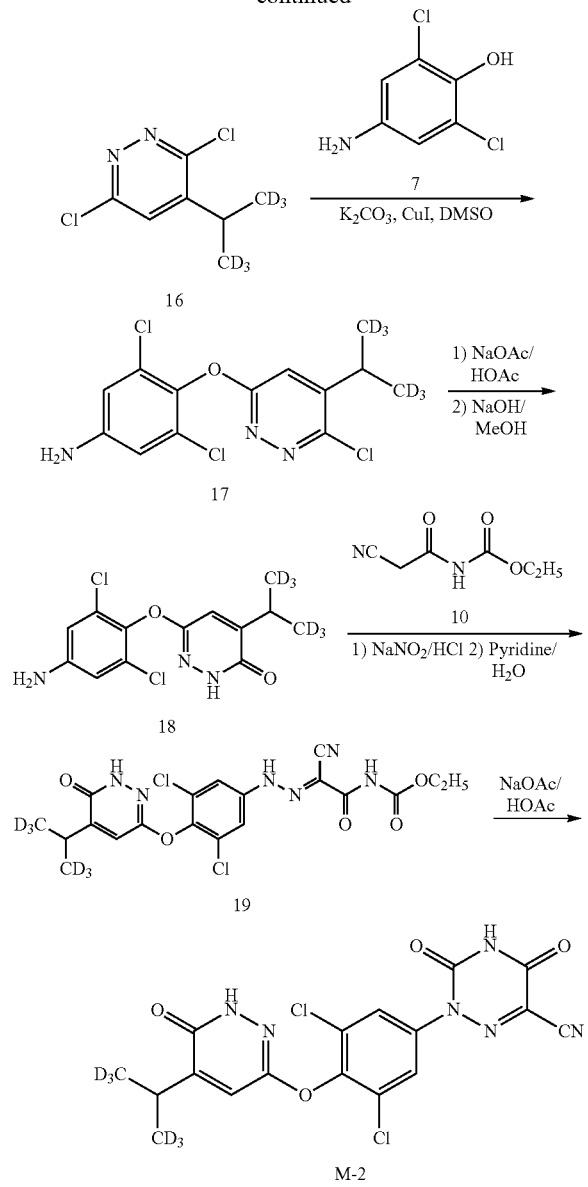

Step 1 Synthesis of Compound 13

Compound 12 (4.0 g, 25.0 mmol) and sodium ethoxide (4.0 g, 57.5 mmol) were sequentially added to ethanol (30 ml). After stirring at 70° C. for 0.5 h, the resulting solution was cooled to room temperature. Then deuterated iodomethane (8.0 g, 55.0 mmol) was slowly added dropwise to the solution described above, and the reaction solution was stirred and reacted at room temperature for 20 h. Most of the solvent was removed, and the residue was extracted with dichloromethane (50 ml×2). The organic phases were combined, and dried over anhydrous sodium sulfate. The solvent was removed to give 3.8 g of brownish red oil, with a yield of 78%.

Step 2 Synthesis of Compound 14

Potassium hydroxide (2.1 g, 38.7 mmol) was added to a solution of compound 13 (3.0 g, 15.5 mmol) in water (20 ml). After refluxing at 100° C. for 3 h, the reaction solution was cooled to room temperature. The pH value of the reaction solution was adjusted to around 2 with concentrated hydrochloric acid. Most of the water was dried with a rotary evaporator, and the residue was extracted with acetone (60 ml×3). The organic phases were combined, and dried over anhydrous sodium sulfate. The solvent was removed to give 1.6 g of an off-white solid, with a yield of 76%.

Step 3 Synthesis of Compound 15

At room temperature, concentrated hydrochloric acid (30 ml) was slowly added to compound 14 (1.6 g, 11.6 mmol), and the resulting solution was heated to 100° C. and refluxed for 12 h. The reaction solution was extracted with dichloromethane (50 ml×3). The organic phases were combined, and dried over anhydrous sodium sulfate. The solvent was removed to give 0.6 g of brown oil, with a yield of 60%.

Step 4 Synthesis of Compound 16

Silver nitrate (0.08 g, 0.473 mmol), compound 15 (0.58 g, 6.15 mmol) and trifluoroacetic acid (0.1 ml) were sequentially added to a solution of compound 5 (0.7 g, 4.73 mmol) in water (20 ml), and the reaction solution was heated to 70° C. Then a solution of ammonium persulfate (2.1 g, 9.46 mmol, 10 ml) in water was slowly added dropwise, after which, the resulting mixture was reacted for 0.5 h, and extracted with dichloromethane (30 ml×3). The organic phases were combined, and dried over anhydrous sodium sulfate. The solvent was removed to give 0.75 g of oil, with a yield of 80%. LC-MS (APCI): m/z=197.09 (M+1)$^+$.

Step 5 Synthesis of Compound 17

Compound 16 (0.7 g, 3.55 mmol), compound 7 (0.62 g, 3.55 mmol), copper(I) iodide (0.41 g, 2.13 mmol) and potassium carbonate (1.90 g, 14.12 mmol) were sequentially added to DMSO (20 ml), and the reaction solution was reacted at 90° C. for 20 h. After cooling to room temperature, water (50 ml) was added to quench the reaction, and the resulting mixture was extracted with ethyl acetate (60 ml×3). The organic phases were combined, and dried over anhydrous sodium sulfate. The solvent was removed, and the concentrate was separated by column (eluent: petroleum ether/ethyl acetate (v/v)=5:1) to give 0.8 g of an off-white solid, with a yield of 67%. LC-MS (APCI): m/z=338.65 (M+1)$^+$.

Step 6 Synthesis of Compound 18

Sodium acetate (0.41 g, 4.80 mmol) was added to a solution of compound 17 (0.8 g, 2.40 mmol) in acetic acid (20 ml), and the reaction solution was reacted at 100° C. for 10 h. After cooling to room temperature, most of the solvent was dried with a rotary evaporator, and the resulting solution was extracted with ethyl acetate (30 ml×2). The organic phases were combined, dried over anhydrous sodium sulfate, and dried with a rotary evaporator to give an intermediate. Then, sodium hydroxide (20 ml, 1 mol/L) and methanol (20 ml) were added, and the reaction solution was refluxed for 12 h. After cooling to room temperature, most of the solvent was removed, and the pH was adjusted to 5 with dilute hydrochloric acid. Ethyl acetate (30 ml×2) was added for extraction. The organic phases were combined, and the concentrate was separated by column (eluent: petroleum ether/ethyl acetate (v/v)=1:1) to give 0.56 g of an off-white solid, with a yield of 74%. LC-MS (APCI): m/z=320.20 (M+1)$^+$. $^1$H NMR (400 MHz, DMSO-$d_6$) δ 12.12 (s, 1H), 7.25 (s, 1H), 6.65 (s, 2H), 5.61 (s, 2H), 2.97 (s, 1H).

Step 7 Synthesis of Compound 19

Compound 18 (0.5 g, 1.58 mmol) and concentrated hydrochloric acid (7 ml) were sequentially added to water (15 ml). The resulting solution was cooled to 0° C., to which a solution of sodium nitrite (0.143 g, 2.05 mmol, 2 ml) in water was slowly added dropwise, and reacted for 0.5 h. In another reactor, compound 10 (0.246 g, 1.58 mmol), pyridine (5 ml) and water (15 ml) were added, and the resulting solution was cooled to 0° C. Then, the reaction solution in the previous reactor was quickly poured into it, stirred and reacted for 0.5 h. After the reaction was completed, ethyl acetate (30 ml×2) was added for extraction. The organic phases were combined, dried, and dried with a rotary evaporator to give 0.48 g of an orange solid, with a yield of 63%. LC-MS (APCI): m/z=487.33 (M+1)+.

Step 8 Synthesis of Compound M-2

Sodium acetate (0.34 g, 4.44 mmol) was added to a solution of compound 19 (0.4 g, 0.82 mmol) in acetic acid (15 ml), and the reaction solution was reacted at 120° C. for 2 h. After cooling to room temperature, most of the solvent was dried with a rotary evaporator. A small amount of water was added and ethyl acetate (20 ml×2) was added for extraction. The organic phases were combined, dried over anhydrous sodium sulfate, and dried with a rotary evaporator to give a crude product. Then activated carbon (0.4 g) and acetonitrile (20 ml) were added, and refluxed for 2 hours. The resulting mixture was cooled, filtered, and dried with a rotary evaporator to give 0.15 g of a product, with a yield of 42%. LC-MS (APCI): m/z=441.26 (M+1)+. $^1$H NMR (400 MHz, DMSO-$d_6$) δ 13.12 (s, 1H), 12.32 (s, 1H), 7.55 (s, 2H), 7.15 (s, 1H), 3.05 (s, 1H).

Example 3 Preparation of 2-(3,5-dichloro-4-((6-oxo-5-(propan-2-yl-1,1,1,3,3,3-$d_6$)-1,6-dihydro-pyridazin-3-yl)oxy)phenyl-2,6-$d_2$)-3,5-dioxo-2,3,4,5-tetrahydro-1,2,4-triazine-6-carbonitrile (Compound M-3)

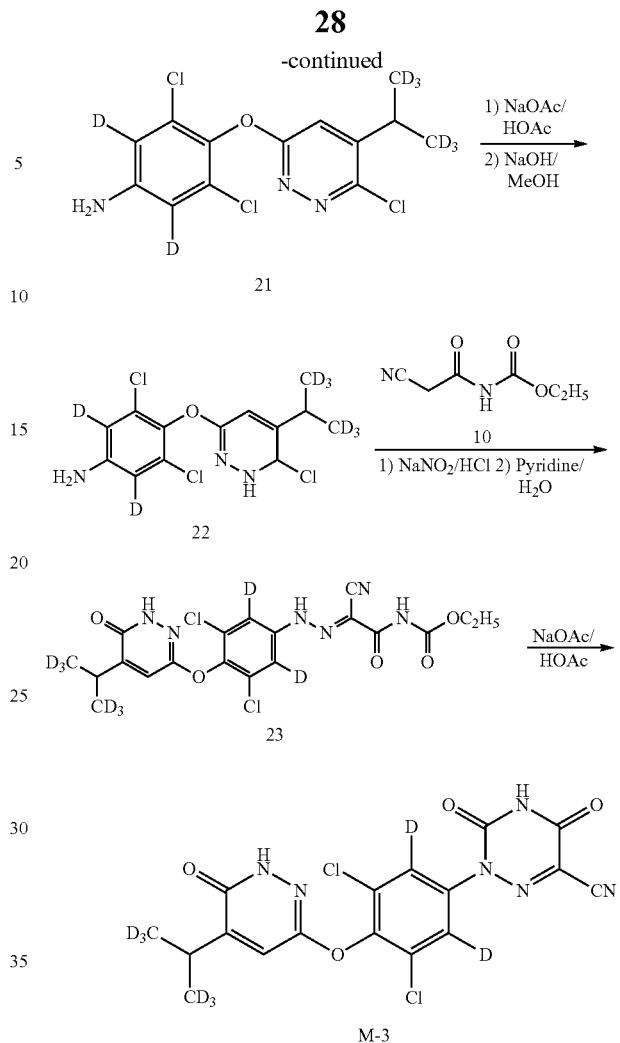

The following route was used for the synthesis:

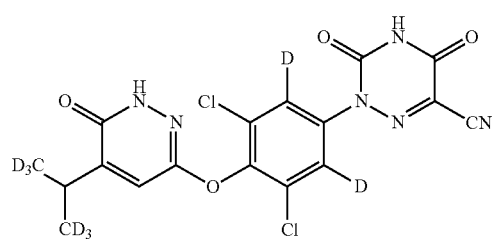

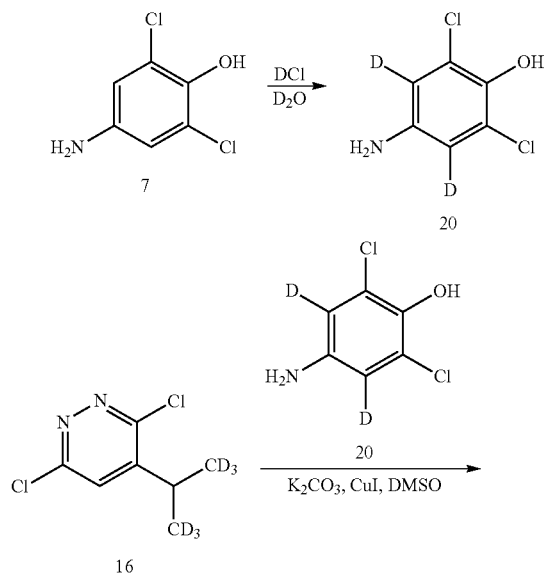

Step 1 Synthesis of Compound 20

Compound 7 (2.0 g, 11.2 mmol) and deuterium chloride (0.52 g, 13.5 mmol) were sequentially added to the heavy water (15 ml) solution. The reaction solution was stirred and reacted in microwave at 180° C. for 0.5 h, and cooled to room temperature. The pH value of the reaction was adjusted to around 7 with sodium carbonate solution, and ethyl acetate (30 ml×2) was added for extraction. The organic phases were washed twice with the saturated sodium chloride solution, after which the organic phases were collected, and dried over anhydrous sodium sulfate. The solvent was removed to give 1.5 g of a reddish brown liquid, with a yield of 75%.

Step 2 Synthesis of Compound 21

Compound 16 (1.0 g, 5.07 mmol), compound 20 (0.91 g, 5.07 mmol), copper(I) iodide (0.57 g, 3.04 mmol) and potassium carbonate (2.79 g, 20.28 mmol) were sequentially added to DMSO (20 ml), and the reaction solution was reacted at 90° C. for 20 h. After cooling to room temperature, water (50 ml) was added to quench the reaction, and the resulting mixture was extracted with ethyl acetate (60 ml×3). The organic phases were combined, and dried over anhydrous sodium sulfate. The solvent was removed, and the concentrate was separated by column (eluent: petroleum ether/ethyl acetate (v/v)=5:1) to give 0.95 g of an off-white solid, with a yield of 56%. LC-MS (APCI): m/z=341.05 (M+1)+.

Step 3 Synthesis of Compound 22

Sodium acetate (0.25 g, 2.94 mmol) was added to a solution of compound 21 (0.5 g, 1.47 mmol) in acetic acid (20 ml), and the reaction solution was reacted at 100° C. for 10 h. After cooling to room temperature, most of the solvent was dried with a rotary evaporator, and the resulting solution was extracted with ethyl acetate (30 ml×2). The organic phases were combined, dried over anhydrous sodium sulfate, and dried with a rotary evaporator to give an intermediate. Then, sodium hydroxide (20 ml, 1 mol/L) and methanol (20 ml) were added, and the reaction solution was refluxed for 12 h. After cooling to room temperature, most of the solvent was removed, and the pH of the residue was adjusted to 5 with dilute hydrochloric acid. Ethyl acetate (30 ml×2) was added for extraction. The organic phases were combined, and the concentrate was separated by column (eluent: petroleum ether/ethyl acetate (v/v)=1:1) to give 0.38 g of an off-white solid, with a yield of 80%. LC-MS (APCI): m/z=322.14 (M+1)$^+$.

Step 4 Synthesis of Compound 23

Compound 22 (0.5 g, 1.57 mmol) and concentrated hydrochloric acid (7 ml) were sequentially added to water (15 ml). The resulting solution was cooled to 0° C., to which a solution of sodium nitrite (0.143 g, 2.05 mmol, 2 ml) in water was slowly added dropwise, and reacted for 0.5 h. In another reactor, compound 10 (0.246 g, 1.57 mmol), pyridine (5 ml) and water (15 ml) were added, and the resulting solution was cooled to 0° C. Then, the reaction solution in the previous reactor was quickly poured into it, stirred and reacted for 0.5 h. After the reaction was completed, ethyl acetate (30 ml×2) was added for extraction. The organic phases were combined, dried, and dried with a rotary evaporator to give 0.4 g of an orange solid, with a yield of 53%. LC-MS (APCI): m/z=489.11 (M+1)$^+$.

Step 5 Synthesis of Compound M-3

Sodium acetate (0.34 g, 4.44 mmol) was added to a solution of compound 23 (0.4 g, 0.82 mmol) in acetic acid (15 ml), and the reaction solution was reacted at 120° C. for 2 h. After cooling to room temperature, most of the solvent was dried with a rotary evaporator. A small amount of water was added and ethyl acetate (20 ml×2) was added for extraction. The organic phases were combined, dried over anhydrous sodium sulfate, and dried with a rotary evaporator to give a crude product. Then activated carbon (0.4 g) and acetonitrile (20 ml) were added, and refluxed for 2 hours. The resulting mixture was cooled, filtered, and dried with a rotary evaporator to give 0.1 g of a product, with a yield of 28%. LC-MS (APCI): m/z=443.09 (M+1)$^+$. $^1$H NMR (400 MHz, DMSO-d$_6$) δ 13.12 (s, 1H), 12.32 (s, 1H), 7.15 (s, 1H), 3.05 (s, 1H).

Example 4 Preparation of 2-(3,5-dichloro-4-((5-isopropyl-6-oxo-1,6-dihydropyridazin-3-yl)oxy)phenyl-2,6-d$_2$)-3,5-dioxo-2,3,4,5-tetrahydro-1,2,4-triazine-6-carbonitrile (Compound M-4)

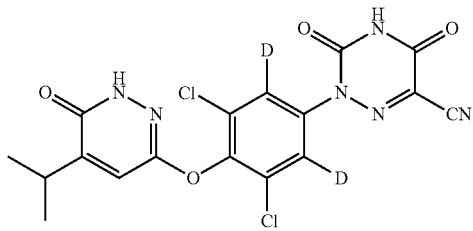

M-4

The following route was used for the synthesis:

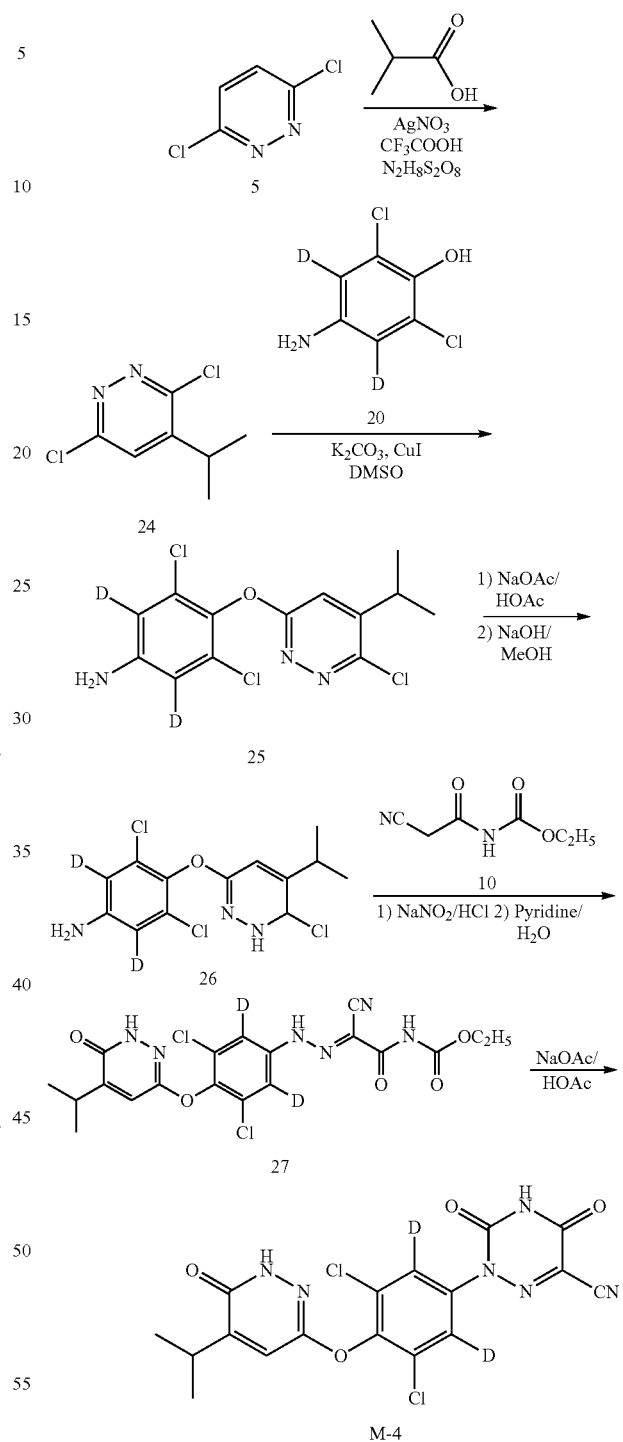

Step 1 Synthesis of Compound 24

Silver nitrate (0.16 g, 0.94 mmol), isobutyric acid (1.16 g, 12.3 mmol) and trifluoroacetic acid (0.2 ml) were sequentially added to a solution of compound 5 (1.4 g, 9.4 mmol) in water (30 ml), and the reaction solution was heated to 70° C. Then a solution of ammonium persulfate (4.2 g, 18.8 mmol, 20 ml) in water was slowly added dropwise, after which, the resulting mixture was reacted for 0.5 h, and extracted with dichloromethane (30 ml×3). The organic phases were combined, and dried over anhydrous sodium sulfate. The solvent was removed to give 1.6 g of oil, with a yield of 88%. LC-MS (APCI): m/z=191.22 (M+1)⁺.

Step 2 Synthesis of Compound 25

Compound 24 (1.05 g, 5.33 mmol), compound 20 (0.93 g, 5.33 mmol), copper(I) iodide (0.61 g, 3.2 mmol) and potassium carbonate (2.85 g, 21.12 mmol) were sequentially added to DMSO (20 ml), and the reaction solution was reacted at 90° C. for 20 h. After cooling to room temperature, water (50 ml) was added to quench the reaction, and the resulting mixture was extracted with ethyl acetate (60 ml×3). The organic phases were combined, and dried over anhydrous sodium sulfate. The solvent was removed, and the concentrate was separated by column (eluent: petroleum ether/ethyl acetate (v/v)=5:1) to give 1.3 g of an off-white solid, with a yield of 74%. LC-MS (APCI): m/z=334.31 (M+1)⁺.

Step 3 Synthesis of Compound 26

Sodium acetate (0.49 g, 6.0 mmol) was added to a solution of compound 25 (1.0 g, 3.0 mmol) in acetic acid (20 ml), and the reaction solution was reacted at 100° C. for 10 h. After cooling to room temperature, most of the solvent was dried with a rotary evaporator, and the resulting solution was extracted with ethyl acetate (30 ml×2). The organic phases were combined, dried over anhydrous sodium sulfate, and dried with a rotary evaporator to give an intermediate. Then, sodium hydroxide (20 ml, 1 mol/L) and methanol (20 ml) were added, and the reaction solution was refluxed for 12 h. After cooling to room temperature, most of the solvent was removed, and the pH of the residue was adjusted to 5 with dilute hydrochloric acid. Ethyl acetate (30 ml×2) was added for extraction. The organic phases were combined, and the concentrate was separated by column (eluent: petroleum ether/ethyl acetate (v/v)=1:1) to give 0.60 g of an off-white solid, with a yield of 63%. LC-MS (APCI): m/z=316.19 (M+1)⁺.

Step 4 Synthesis of Compound 27

Compound 26 (0.5 g, 1.58 mmol) and concentrated hydrochloric acid (7 ml) were sequentially added to water (15 ml). The resulting solution was cooled to 0° C., to which a solution of sodium nitrite (0.143 g, 2.05 mmol, 2 ml) in water was slowly added dropwise, and reacted for 0.5 h. In another reactor, compound 10 (0.246 g, 1.58 mmol), pyridine (5 ml) and water (15 ml) were added, and the resulting solution was cooled to 0° C. Then, the reaction solution in the previous reactor was quickly poured into it, stirred and reacted for 0.5 h. After the reaction was completed, ethyl acetate (30 ml×2) was added for extraction. The organic phases were combined, dried, and dried with a rotary evaporator to give 0.55 g of an orange solid, with a yield of 72%. LC-MS (APCI): m/z=483.52 (M+1)⁺.

Step 5 Synthesis of Compound M-4

Sodium acetate (0.47 g, 5.70 mmol) was added to a solution of compound 27 (0.55 g, 1.13 mmol) in acetic acid (15 ml), and the reaction solution was reacted at 120° C. for 2 h. After cooling to room temperature, most of the solvent was dried with a rotary evaporator. A small amount of water was added and ethyl acetate (20 ml×2) was added for extraction. The organic phases were combined, dried over anhydrous sodium sulfate, and dried with a rotary evaporator to give a crude product. Then activated carbon (0.4 g) and acetonitrile (20 ml) were added, and refluxed for 2 hours. The resulting mixture was cooled, filtered, and dried with a rotary evaporator to give 0.2 g of a product, with a yield of 40%. LC-MS (APCI): m/z=437.16 (M+1)⁺. ¹H NMR (400 MHz, DMSO-d₆) δ 13.15 (s, 1H), 12.52 (s, 1H), 7.05 (s, 1H), 3.05 (s, 1H). 1.18 (d, 6H).

Biological Activity Assay (1) TRβ Binding Experiment

Reagents and Materials:

Biotin-SRC2-2 coactivator peptide (Sangon Biotech), TRβLBD, GST (Invitrogen, Cat. No. PV4764), europium-labeled anti-GST (Cisbio, Cat. No. 61GSTKLB), streptavidin-D2 (Cisbio, Cat. No. 610SADAB), DTT (Invitrogen, Cat. No. P2325), DMSO (Sigma, Cat. No. D8418), T3 (MCE, Cat. No. HY-A0070), 96-well plate (Nunc, Cat. No. 249944), 384-well plate (Greiner, Cat. No. 784076).

Specific Experimental Protocol:

Preparation of reaction buffer solution: A 50 mM Tris-HCl buffer solution (pH 7.4) containing 100 mM NaCl, 1 mM EDTA, 50 mM KF, 1 mM DTT, 1 mM MgCl₂, 10% glycerol, 0.01% NP-40 and 0.1% BSA was prepared.

Compounds assay: a) 10 μM Ref (T3) or 1 mM compounds were prepared in DMSO; b) T3 and the compounds were subjected to a 3-fold serial gradient dilution in DMSO from 10 μM and 1 mM, respectively, and 10 doses were obtained in a 96-well plate; c) each of the 100× compounds was diluted to 4× using a serial gradient dilution d) 5 ul of the serial gradient dilutions of the compounds were added to a 384-well plate; e) 5 ul of TRβLBD was added to the assay plate; f) 10 ul of a solution (containing 400 nM biotin-SCC2-2, anti-GST-Eu and 50 nM avidin-d2) was added to each well of the assay plate to start the reaction; g) the plate was incubated at room temperature for 3 hours protected from light; h) the plate was read at wavelengths of 665 nm and 615 nm with a Envision 2104 plate reader.

Data Analysis:

a) The ratio (Ratio 665 nm/615 nm-Ratio background) of each well was calculated;

b) The % activity was calculated according to the following formula:

$$\% \text{ Activity} = \left[ \frac{\text{Ratio}_{cmpd} - \overline{\text{Ratio}}_{Vehicle}}{\overline{\text{Ratio}}_{Positive} - \overline{\text{Ratio}}_{Vehicle}} \right] * 100$$

$\overline{\text{Ratio}}_{positive}$: The average ratio of the positive controls in the entire plate, $\overline{\text{Ratio}}_{vehicle}$: The average ratio of the negative controls in the entire plate;

c) EC₅₀ was calculated by fitting the values of % activity and the logarithm of the compound concentrations to the nonlinear regression (dose response-variable slope) with Graphpad 5.0, wherein A means that EC₅₀≤200 nM, B means that EC₅₀ is from 200 to 500 nM, C means that EC₅₀ is from 500 to 1000 nM, and D means that EC₅₀>1000 nM.

In the TRβ binding experiment described above, EC₅₀ values of the compounds disclosed herein were tested. As shown in Table 1 below, the compounds of the present disclosure are thyroid hormone receptor agonists.

TABLE 1

| Example compound | EC₅₀ (nM) |
| --- | --- |
| MGL-3196 | B |
| Compound M-1 | B |
| Compound M-2 | B |
| Compound M-3 | B |
| Compound M-4 | B |

(2) Metabolic Stability Evaluation

Microsome assay: human liver microsomes: 0.5 mg/mL, Xenotech; rat liver microsomes: 0.5 mg/mL, Xenotech;

coenzyme (NADPH/NADH): 1 mM, Sigma Life Science; magnesium chloride: 5 mM, 100 mM phosphate buffer (pH 7.4).

Preparation of stock solutions: Powder of the example compounds were accurately weighed and dissolved in DMSO to 5 mM respectively.

Preparation of phosphate buffer (100 mM, pH7.4): A pre-prepared 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 µL of phosphate buffer (pH 7.4) was taken into a 50 mL centrifuge tube, to which 812.5 µL of human liver microsomes were added, and mixed to obtain a liver microsome dilution with a protein concentration of 0.625 mg/mL. 25057.5 µL of phosphate buffer (pH 7.4) was taken into a 50 mL centrifuge tube, to which 812.5 µL of SD rat liver microsomes were added, and mixed to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 µL of the dilutions of human liver microsomes and rat liver microsomes were added to 96-well incubation plates (N=2), respectively, and 2 µL of 0.25 mM working solution was added respectively and mixed.

Metabolic stability assay: 300 µL of pre-chilled stop solution was added to each well of 96-well deep well plates and placed on ice as stop plates. The 96-well incubation plates and NADPH regeneration system were placed in a 37° C. water bath, shaken at 100 rpm and pre-incubated for 5 min. 80 µL of incubation solution was taken out from each well of the incubation plates and added to the stop plates, mixed, and replenished with 20 µL of NADPH regeneration system solution as a 0-min sample. 80 µL of NADPH regeneration system solution was added to each well of the incubation plates to start the reaction and start counting. The corresponding compounds had a reaction concentration of 1 µM and the protein concentration was 0.5 mg/mL. Separately, 100 µL of the reaction solutions was taken at 10, 30, and 90 min after the reaction, respectively, added to stop plates, and vortexed for 3 minutes to terminate the reaction. The stop plates were centrifuged at 5000×g at 4° C. for 10 min. 100 µL of the supernatant was added to a 96-well plate to which 100 µL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of remaining compound versus time, and $t_{1/2}$ and $CL_{int}$ were calculated according to the equation below, where V/M equals to 1/protein concentration $$t_{1/2} = -\frac{0.693}{\text{slope}}, CL_{int} = \frac{0.693}{t_{1/2}} \cdot \frac{V}{M} t_{1/2}(\text{min}); CL_{int}(\mu L/\text{min/mg}).$$

The metabolic stability of the compounds in human and rat liver microsomes was evaluated by simultaneously testing and comparing the compounds disclosed herein and the non-deuterated compound. The values of $t_{1/2}$ and $CL_{int}$ of the representative example compounds are shown in Table 2 below. The non-deuterated compound MGL-3196 was used as a control sample. In the human and rat liver microsome assays, compared with the non-deuterated compound MGL-3196, the compounds of the present disclosure can significantly improve the metabolic stability.

TABLE 2

| Example compound | Human liver microsome | |
|---|---|---|
| | $t_{1/2}$(min) | $CL_{int}$(µL/min/mg)) |
| MGL-3196 | <500 | 2.5~3.0 |
| Compound M-1 | >1000 | 0.1~2.0 |
| Compound M-2 | >1000 | 0.1~2.0 |
| Compound M-3 | >1000 | 0.1~2.0 |
| Compound M-4 | >1000 | 0.1~2.0 |

(3) Pharmacokinetic Experiment in Rats

Six male Sprague-Dawley rats, 7 to 8 weeks old, weighing approximately 210 g, were divided into 2 groups with 3 rats in each group. The pharmacokinetic differences of the compounds were compared after they were administered to the rats at a single dose through vein or mouth (orally 10 mg/kg).

The rats were fed with standard feed and water, and fasted 16 hours before the experiment. The drugs were dissolved with PEG400 and dimethyl sulfoxide. The blood samples were collected from eyelids at the time point of 0.083, 0.25, 0.5, 1, 2, 4, 6, 8, 12 and 24 hours after administration.

The rats were anesthetized for a short time after inhaling ether, and 300 µL of blood samples was collected from the eyelids and put into test tubes, which contain 30 µL of 1% heparin salt solution. The test tubes were dried overnight at 60° C. prior to use. After the blood sample collection at the last time point, the rats were sacrificed after the ether anesthesia.

Immediately after the collection of the blood samples, the test tubes were gently inverted at least 5 times to ensure the fully mixing and placed on ice. The blood samples were centrifuged at 4° C., 5000 rpm for 5 minutes to separate the plasma from the red blood cells. 100 µL of plasma was pipetted into a clean plastic centrifuge tube, with the name of the compound and time point on it. The plasma was stored at −80° C. before analysis, and LC-MS/MS was used to determine the concentration of the compounds disclosed herein in plasma. Pharmacokinetic parameters were calculated based on the plasma concentrations of each animal at different time points.

The experiment shows that the compounds disclosed herein have better pharmacokinetic properties in animals, and therefore have better pharmacodynamics and therapeutic effects.

The above content is a further detailed description disclosed herein in combination with specific preferred embodiments, and it cannot be assumed that the specific implementation disclosed herein is limited to these descriptions. For a person of ordinary skill in the art to which the present disclosure pertains, a number of simple deductions or substitutions can be made without departing from the concept disclosed herein, and should all be considered as falling within the protection scope disclosed herein.

The invention claimed is:

1. A compound of formula (I), or a pharmaceutically acceptable salt, prodrug, hydrate, solvate, crystal form, stereoisomer or isotopic variant thereof:

Formula (I)

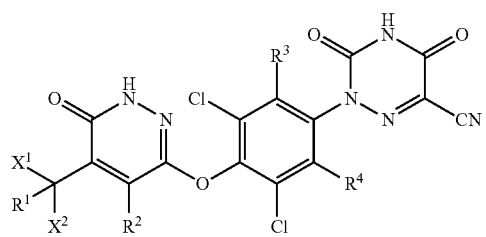

wherein,
$R^1$ and $R^2$ are hydrogen;
$R^3$ and $R^4$ are independently selected from hydrogen and deuterium;
$X^1$ and $X^2$ are independently selected from $CH_3$, $CD_3$, $CHD_2$ and $CH_2D$;
with the proviso that if $X^1$ and $X^2$ are both $CH_3$, then at least one of $R^3$ and $R^4$ is deuterium.

2. The compound, pharmaceutically acceptable salt, prodrug, hydrate, solvate, crystal form, stereoisomer or isotopic variant thereof according to claim 1, wherein $R^3$ and $R^4$ are hydrogen.

3. The compound, pharmaceutically acceptable salt, prodrug, hydrate, solvate, crystal form, stereoisomer or isotopic variant thereof according to claim 1, wherein $X^1$ is $CD_3$.

4. The compound, pharmaceutically acceptable salt, prodrug, hydrate, solvate, crystal form, stereoisomer or isotopic variant thereof according to claim 1, wherein $X^2$ is $CD_3$.

5. The compound, or the pharmaceutically acceptable salt, prodrug, hydrate, solvate, crystal form, stereoisomer or isotopic variant thereof according to claim 1, wherein the compound is selected from the following compounds:

Formula (2)

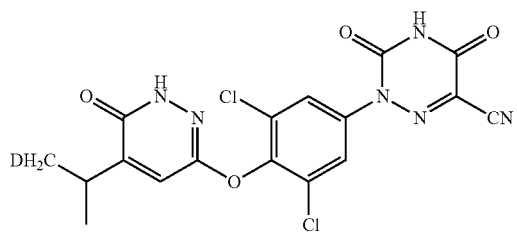

Formula (3)

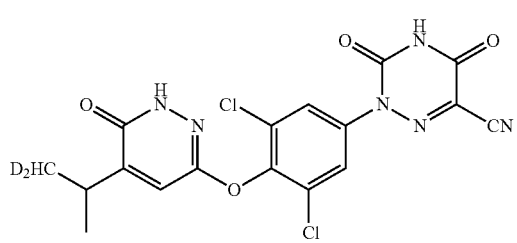

Formula (4)

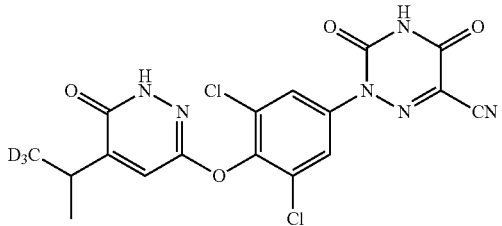

Formula (5)

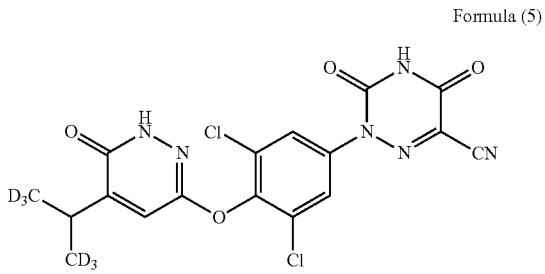

Formula (9)

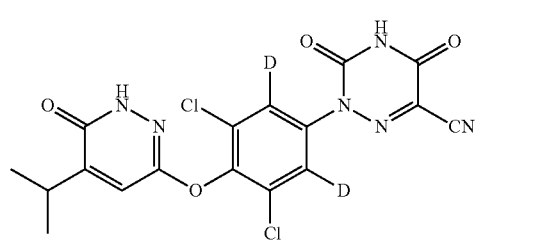

Formula (10)

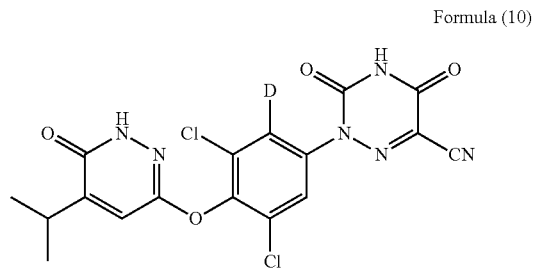

Formula (11)

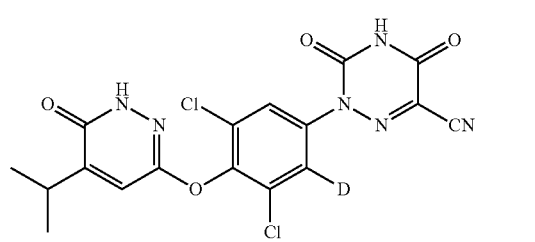

Formula (13)

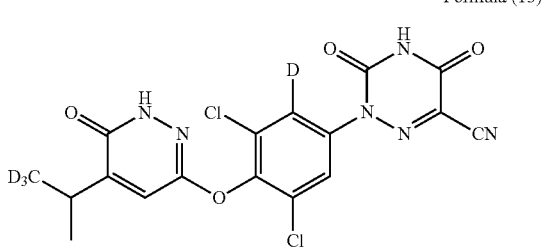

Formula (14)
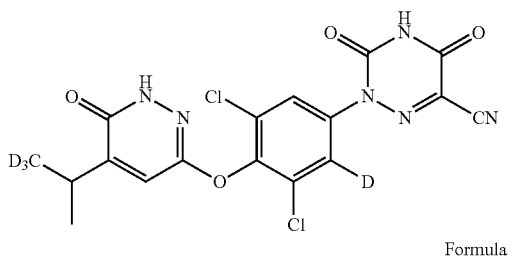
Formula (15)
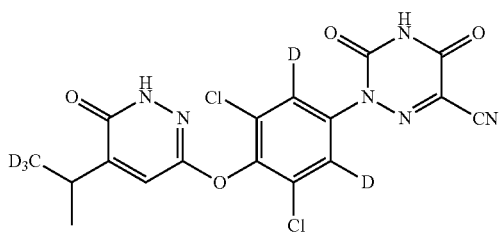
Formula (16)
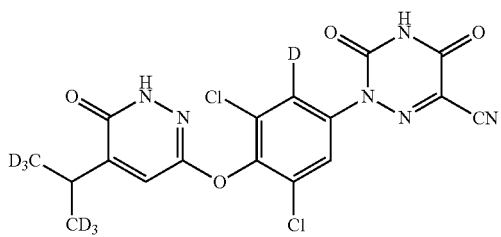
Formula (17)
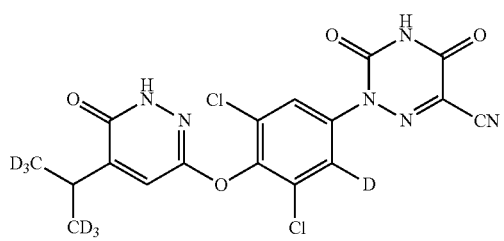
Formula (18)
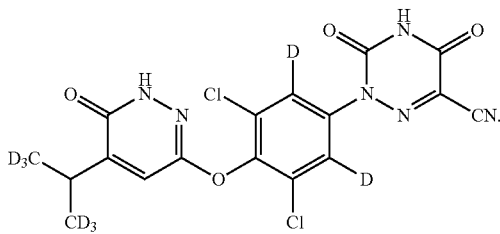
6. A pharmaceutical composition, comprising pharmaceutically acceptable excipient(s) and the compound, or the pharmaceutically acceptable salt, prodrug, hydrate, solvate, crystal form, stereoisomer or isotopic variant thereof according to claim 1.
* * * * *